(12) United States Patent
Kamahori et al.

(10) Patent No.: US 8,323,468 B2
(45) Date of Patent: Dec. 4, 2012

(54) ION CONCENTRATION MEASURING DEVICE AND ION CONCENTRATION MEASURING ELEMENT

(75) Inventors: Masao Kamahori, Kokubunji (JP); Yu Ishige, Tokyo (JP); Kotaro Yamashita, Mito (JP); Yasuhisa Shibata, Hitachiomiya (JP); Masafumi Miyake, Hitachinaka (JP)

(73) Assignee: Hitachi-High Technologies Corporation, Tokyo (JP)

( * ) Notice: Subject to any disclaimer, the term of this patent is extended or adjusted under 35 U.S.C. 154(b) by 1081 days.

(21) Appl. No.: 12/081,736

(22) Filed: Apr. 21, 2008

(65) Prior Publication Data

US 2008/0264790 A1    Oct. 30, 2008

(30) Foreign Application Priority Data

Apr. 27, 2007    (JP) ................. 2007-118640

(51) Int. Cl.
*G01N 27/333* (2006.01)
(52) U.S. Cl. ............. 204/416; 205/789; 257/253
(58) Field of Classification Search ........... 204/403.01–403.15, 419; 257/253; 205/777.5, 778, 792, 205/789
See application file for complete search history.

(56) References Cited

U.S. PATENT DOCUMENTS

| | | | |
|---|---|---|---|
| 2005/0170347 A1* | 8/2005 | Miyahara et al. | 435/6 |
| 2008/0185288 A1* | 8/2008 | Yokokawa | 204/418 |
| 2009/0071826 A1* | 3/2009 | Kamahori et al. | 204/418 |

FOREIGN PATENT DOCUMENTS

| | | |
|---|---|---|
| EP | 1 619 496 A1 | 3/2005 |
| WO | WO 2006/113440 | 4/2006 |

OTHER PUBLICATIONS

Extended European Search Report dated Aug. 25, 2008 regarding European Application No. 08007849.6-2204.
Reinhoudt, D.N., "Molecular Recognition Applied to Sensors", Elsevier Science S.A. Sensors and Actuators B Chemical, vol. 24-25, 1995, pp. 33-35.
Flink, Simon, et al., "Sensor Functionalities in Self-Assembled Monolayers" Advanced Materials, vol. 12, No. 18, Sep. 15, 2000, pp. 1315-1328.
Simon Flink et al., "Electrochemical Detection of Electrochemically Inactive Cations by Self-Assembled Monolayers of Crown Ethers", J. Am. Chem. Soc. vol. 120, (1998), pp. 4652-4657.
Nantanit Wanichacheva et al., "Surface-Based Lithium Ion Sensor: An Electrode Derivatized with a Self-Assembled Monolayer", Anal. Chem., No. 78 (2006), pp. 7132-7137.

* cited by examiner

Primary Examiner — Kaj K Olsen
Assistant Examiner — Kourtney R Carlson
(74) Attorney, Agent, or Firm — Stites & Harbison, PLLC; Juan Carlos A. Marquez, Esq (57) ABSTRACT

A crown ether derivative that acts as cation capturing ligand and alkanethiol having a longer carbon chain than a linker are immobilized, coexisting together, on the surface of a gold electrode, by using as the linker an insulating molecule (e.g., alkanethiol) that forms self-assembled monolayers. Electromotive force produced in association with cation coordination is measured by a potentiometer through a change in interfacial potential on the surface of the gold electrode. Further, an insulated gate field effect transistor formed on the same substrate as the gold electrode is used as the potentiometer. Furthermore, a straight-chain polymer physically adsorbed on the gold electrode is used in order to reduce the influence of the adsorption of impurities on the surface of the electrode during biological sample measurement.

15 Claims, 11 Drawing Sheets

FIG. 13B

ION CONCENTRATION MEASURING DEVICE AND ION CONCENTRATION MEASURING ELEMENT

CLAIM OF PRIORITY

The present application claims priority from Japanese application JP 2007-118640 filed on Apr. 27, 2007, the content of which is hereby incorporated by reference into this application.

BACKGROUND OF THE INVENTION

1. Field of the Invention

The present invention relates to an ion concentration measuring device for measuring a cation, particularly a sodium ion or a potassium ion, in a biological sample.

2. Description of the Related Art

Methods for analyzing the concentration of an electrolyte (such as a sodium ion or a potassium ion) in a biological sample, particularly blood serum or blood plasma, include flame photometry and ion selective electrode method. Of these, the ion selective electrode method is now widely used since it can determine ion concentration in a sample only by immersing the ion selective electrode in a sample solution in conjunction with a reference electrode. In the medical field, a device for the ion selective electrode method is built in a biochemical automatic analyzer, taking the advantage that such device can be miniaturized and automated.

A liquid-membrane ion selective electrode has an ion-selective membrane to which an ionophore (or ligand) is added. Each ligand is capable of selectively interacting with a certain ion, and various kinds of ions can be measured with different ligands added to the ion-selective membrane according to the target ions. An ion-sensitive material called a "neutral carrier" is used for a cation selective electrode for the sodium ion, the potassium ion, and the like. Crown ether, which is a typical neutral carrier, selectively recognizes a cation fitted to a hole size of a crown ring. Generally, 12-crown-4 is suitable for a lithium ion; 15-crown-5, for the sodium ion; and 18-crown-6, for the potassium ion. Moreover, crown ether can have better cation selectivity than monocrown ether by sandwiching a cation between two crown rings. In this case, 14-crown-4 is suitable for the sodium ion; and 15-crown-5, for the potassium ion.

Because of the problem of interference made by a lipophilic anion, the ion selective electrode using a crown ether compound additionally contains a plasticizer or an anion excluder mixed with the ligand in polyvinyl chloride (PVC), that acts as a membrane support material. Typically, dioctyl phenyl phosphonate (DOPP) or nitrophenyl octyl ester (NPOE) is used as the plasticizer, and sodium tetraphenylborate that is lipophilic salt is used as the anion excluder. In addition, the ligand has a complex structure with a hydrophobic side chain (for example, a long alkyl chain) added thereto, in order to prevent elution of the ligand from within the lipophilic PVC membrane from deteriorating performance of the ion selective electrode. Since the ion-selective membrane in contact with an internal standard solution is immersed in the sample solution in actual measurement, fabrication of the ion selective electrode requires an operation of attaching an ion-selective membrane to an internal standard solution receptacle, besides an operation of forming the ion-selective membrane.

There has been proposed the ion selective electrode in which the ligand is immobilized on the surface of a gold electrode, in order to solve the above problem with the liquid-membrane ion selective electrode; to simplify the structure and a fabrication method of the ion selective electrode; and to miniaturize an analytical instrument in the future. As an example of a sodium ion selective electrode, it has been reported that a mercapto crown ether compound has been immobilized on the gold electrode as neutral carrier type ligand (See J. Am. Chem. Soc., 120 (1998): 4652-4657). Moreover, as an example of a lithium ion selective electrode, it has also been reported that the neutral carrier type ligand has likewise been immobilized on the surface of the gold electrode, utilizing a bond between thiol and gold (See Anal. Chem., 78 (2006): 7132-7137, and WO2006/113440.)

SUMMARY OF THE INVENTION

The above-described ion selective electrode with the ligand immobilized on the surface of the gold electrode, however, is not designed in consideration of the insulating property of the surface of the gold electrode and the ligand's surrounding environment, and thereby takes impedance measurement rather than potential measurement to obtain a desired ion concentration. The reason is that: the conventional ion selective electrode with the ligand immobilized on the surface of the gold electrode is not designed in consideration of the insulation property between the surface of the gold electrode and a measuring solution, and thus is incapable of stably measuring the interface potential because actual measurement is affected by leakage current at the surface of the electrode. Impedance measurement method includes the steps of: disposing a working electrode and a counter electrode made of gold, platinum or the like, and a reference electrode, for keeping the potential of a counter electrode and the working electrode constant, in the solution; and obtaining frequency response to a voltage applied between the working electrode and the counter electrode, through a current value measurement using a potentiostat that is an electric current measuring instrument. In this method, a redox material that is an electrochemical active substance needs to be added to the measuring solution. This makes it impossible to take the advantage of the conventional ion selective electrode method that the ion concentration in the sample is obtained only by immersing the ion selective electrode together with the reference electrode in the sample solution. Moreover, the impedance measurement method also has the problem of a narrow concentration-measuring range in principle, because this method is a current measurement method.

An object of the present invention is to provide an ion concentration measuring device using a simplified structure and a simplified fabrication method of an ion selective electrode while maintaining basic performance such as a concentration-measuring range, and the advantage that the conventional ion selective electrode method is capable of obtaining the ion concentration in the sample only by immersing the ion selective electrode together with the reference electrode in the sample solution.

In order to attain the above object, according to the present invention, a crown ether derivative that acts as cation capturing ligand is immobilized on the surface of the gold electrode, using as a linker an insulating molecule (for example, alkanethiol) that forms self-assembled monolayers, and electromotive force generated in association with cation coordination is measured as a variation in interfacial potential on the surface of the gold electrode. In this method, if a crown ether ring is larger than a distance between the self-assembled monolayers and thus there is a gap between the immobilized molecules, an insulating molecule (for example, alkanethiol) having a longer carbon chain than that of the linker is immobilized while coexisting with the crown ether derivative. Further, an insulated gate field effect transistor formed on the same substrate as the gold electrode is used as a potentiometer. On that occasion, measurement is performed by superimposing an a.c. voltage of 1 kHz or higher on the reference electrode. Furthermore, a straight-chain polymer is used by physically adsorbed on the gold electrode, so as to reduce the influence caused by the adsorption of impurities on the surface of the electrode during biological sample measurement.

According to the present invention, the insulation property between the gold electrode and the solution may be improved by immobilizing the crown ether derivative that acts as the cation capturing ligand on the surface of the gold electrode through the insulating molecule. The improvement in the insulation property enables suppressing the leakage current at the surface of the electrode, thus stably measuring the electromotive force generated in association with the cation coordination as the variation in the interfacial potential on the surface of the gold electrode. If the crown ether ring is larger than the distance between the self-assembled monolayers, the insulating molecule, such as the alkanethiol having a longer carbon chain than that of the linker is immobilized while coexisting with the crown ether derivative. This enables eliminating the gap between the immobilized molecules thus maintaining the insulation property between the gold electrode and the solution.

Further, by using the insulated gate field effect transistor formed on the same substrate as the gold electrode as the potentiometer, the leakage current may be reduced and thus the interface potential on the surface of the gold electrode may be stably measured. On that occasion, by superimposing an a.c. voltage of 1 kHz or higher on the reference electrode, the interfacial potential on the surface of the gold electrode may be stabilized, and thus measurement accuracy may be improved. In addition, the straight-chain polymer may be used by physically adsorbed on the gold electrode in order to reduce noise or drift caused by the adsorption of the impurities on the surface of the electrode during the biological sample measurement.

DETAILED DESCRIPTION OF THE PREFERRED EMBODIMENTS

Embodiments of the present invention will be described below with reference to the drawings.

Figure 1:
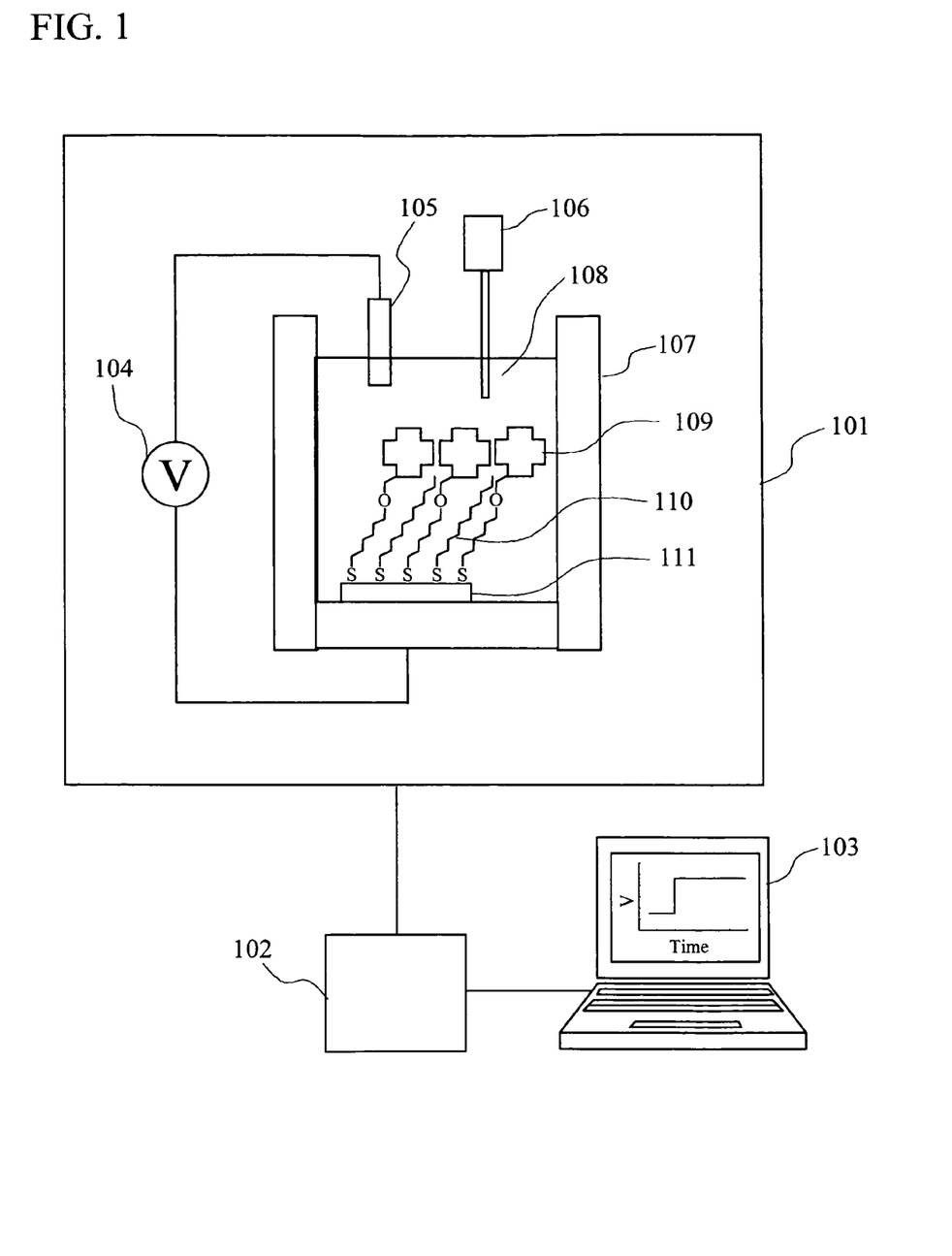
FIG. 1 is a block diagram showing an example of an ion concentration measuring device according to the present invention.
Figure 2A:
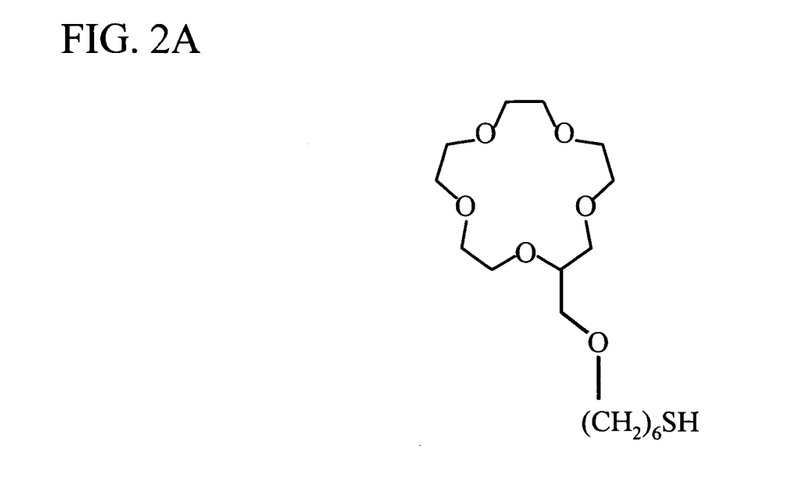
FIGS. 2A to 2C are views showing an example of sodium ion capturing ligand according to the present invention.
Figure 2B:
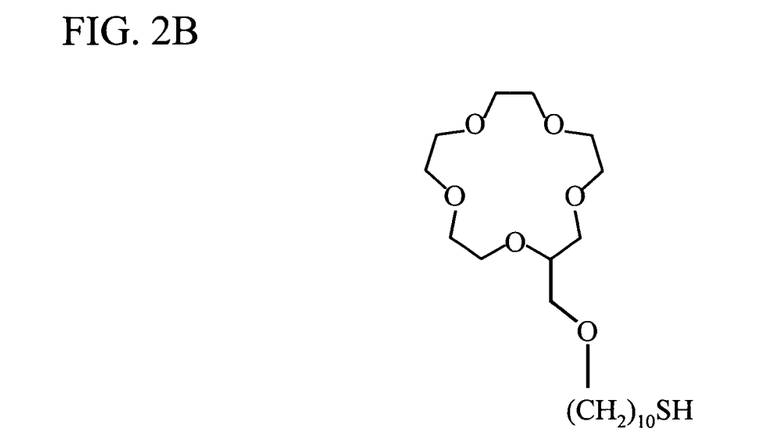
Figure 2C:
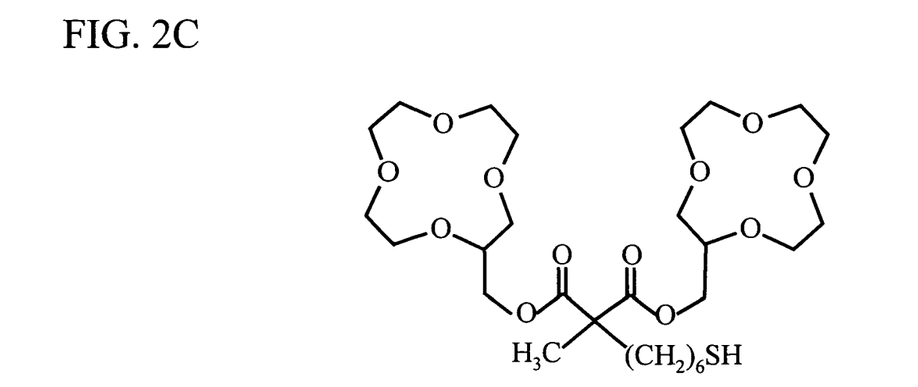

FIG. 1 is a block diagram showing an example of an ion concentration measuring device according to the present invention. The measuring device of the present invention includes a measuring unit 101, a signal processing circuit 102, and a data processor 103. The measuring unit 101 includes a potentiometer 104, a reference electrode 105, a sample injector 106 that provides a sample solution containing a measuring substance, and a measuring cell 107. A gold electrode 111 and the reference electrode 105 are disposed in a measuring solution 108 within the measuring cell 107, and a crown ether derivative 109 that acts as cation capturing ligand, and alkanethiol 110 that acts as an insulating molecule are immobilized on the gold electrode 111. In this example, a 15-crown-5 derivative that is a mono-crown ether derivative is used here as sodium ion capturing ligand. Alternatively, a bis(12-crown-4) derivative that is a bis-crown ether derivative may also be used. 2-[(6-mercaptohexyl)oxy]methyl-(15-crown-5) in which the number of carbon atoms of a linker is six as shown in FIG. 2A, or 2-[10-mercaptodecyl)oxy]methyl-(15-crown-5) in which the number of carbon atoms of the linker is ten as shown in FIG. 2B can be used as the 15-crown-5 derivative; and di(1,4,7,10-tetraoxacyclododecan-2-ylmethyl)methyl(6-sulfanylhexyl) shown in FIG. 2C, as the bis(12-crown-4) derivative. In addition, as to the length of carbon chain of the alkanethiol that acts as the insulating molecule, coexisting on that occasion, there is no problem as long as it is equal to or longer than the length of carbon chain of the linker of the crown ether derivative. For example, if the number of carbon atoms of the linker of the crown ether derivative is six, 6-hexanethiol, 8-octanethiol, 11-undecanethiol, 14-tetradecanethiol or 18-octadecanethiol may be used. Moreover, a 12-crown-4 derivative can be used as lithium ion capturing ligand; and an 18-crown-6 derivative or a bis(15-crown-5) derivative, as potassium ion capturing ligand.

A measuring procedure is as follows. First, the sample solution is filled into the measuring solution 108 within the measuring cell 107 by use of the sample injector 106. A sodium ion that is a measuring object in the sample solution forms complex, through ion-dipole interaction, with the crown ether derivative 109 that acts as the cation capturing ligand, and thus, charge separation occurs between the sodium ion and its counter anion on the surface of the gold electrode 111. This results in a change in interfacial potential on the gold electrode 111. Potential measurement is carried out by making real-time measurement, using the potentiometer 104, of the change in the interfacial potential of the gold electrode 111 before and after the sample solution is filled by the sample injector 106; and thereafter by recording the measured potential-change value by means of the signal processing circuit 102 and the data processor 103. The change in the interfacial potential on the gold electrode 111 depends on the concentration of the sodium ion that is the measuring object. Thus, the sodium ion concentration in the sample of unknown concentration can be obtained from the measured potential-change value, based on a calibration curve prepared beforehand through measurement of a standard solution. A syringe pump or a pressure dispensing device can be used as the sample injector 106. Additionally, an electrode made of other noble metal such as silver or carbon may be used in place of the gold electrode 111. Further, a straight-chain polymer may be used by physically adsorbed on the gold electrode in order to reduce the influence caused by the adsorption of impurities on the surface of the electrode during biological sample measurement. Methyl cellulose, acrylamide, dextran, polyethylene glycol or the like can be used as the straight-chain polymer.

The reference electrode 105 applies a potential to be used as the reference, for the purpose of stably measuring the potential change based on an equilibrium reaction or a chemical reaction that occurs on the surface of the gold electrode 111 in the measuring solution 108. Although a silver/silver chloride electrode using saturated potassium chloride for an internal solution or a calomel electrode is typically used as the reference electrode, there is no problem in using the silver/silver chloride electrode alone as a quasi-electrode, in the case where the sample solution to be measured is of fixed composition.

Figure 3:
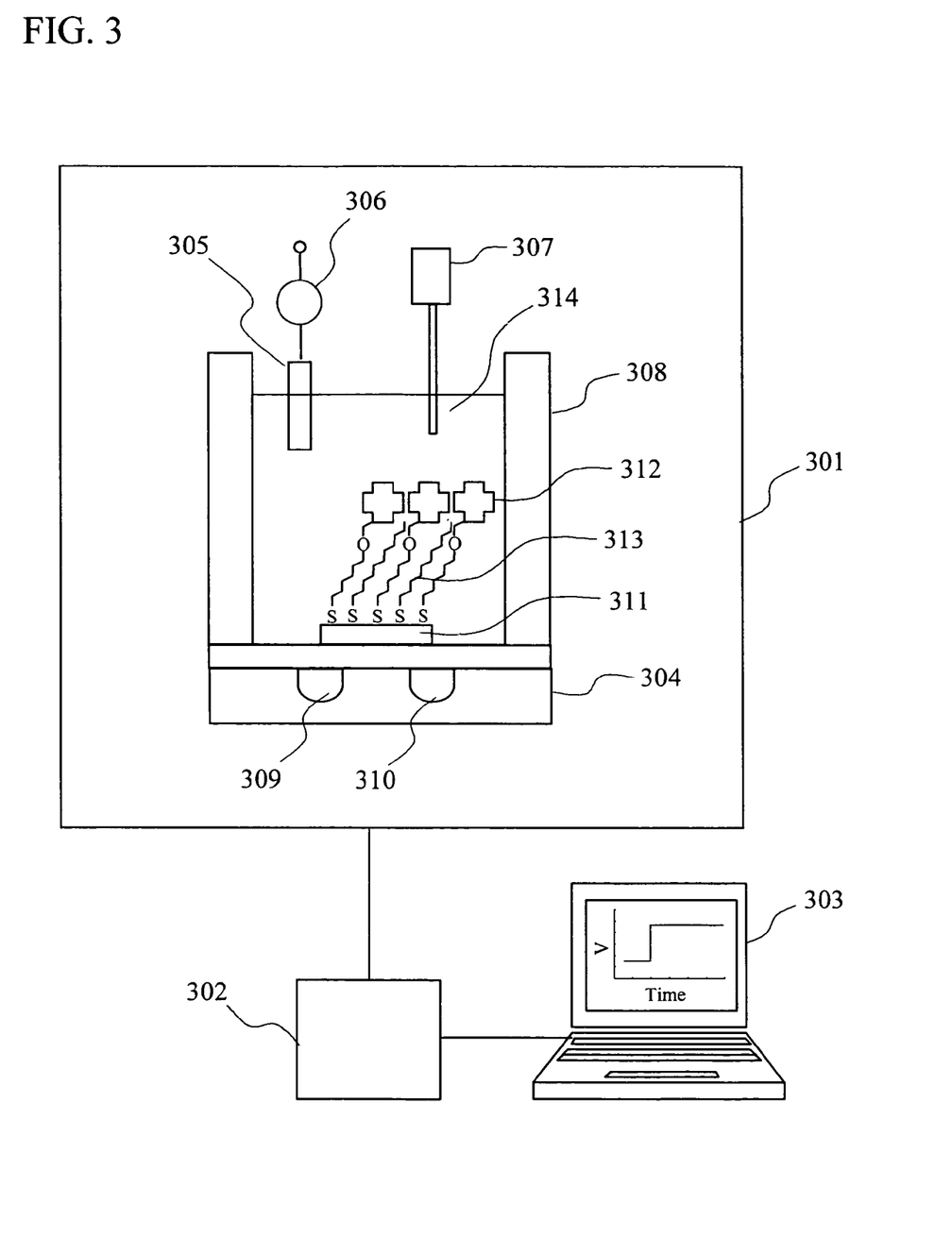
FIG. 3 is a block diagram showing an example of the ion concentration measuring device using a FET sensor according to the present invention.

Other embodiments of the present invention will be described below with reference to the drawings. FIG. 3 is a block diagram showing an example of the ion concentration measuring device according to the present invention, using a field effect transistor (FET) sensor. The measuring device of the present invention includes a measuring unit 301, a signal processing circuit 302, and a data processor 303. The measuring unit 301 includes an insulated gate field effect transistor 304, a reference electrode 305, a power supply 306 that applies a voltage to the reference electrode 305, a sample injector 307 that provides a sample solution containing a measuring substance, and a measuring cell 308. The insulated gate field effect transistor 304 includes a source 309, a drain 310, and a gold electrode 311 having an electrical connection to a gate. Immobilized on the gold electrode 311 are a crown ether derivative 312 that acts as cation capturing ligand, and alkanethiol 313. Disposed in a measuring solution 314 within the measuring cell 308 are the gold electrode 311 with the crown ether derivative 312 that acts as the cation capturing ligand and the alkanethiol 313 immobilized thereon, and the reference electrode 305.

A measuring procedure is as follows. First, the sample solution is filled into the measuring solution 314 within the measuring cell 308 by use of the sample injector 307. A sodium ion that is a measuring object in the sample solution forms complex, through ion-dipole interaction, with the crown ether derivative 312 that acts as the cation capturing ligand, and thus, charge separation occurs between the sodium ion and its counter anion on the surface of the gold electrode 311 formed on the insulated gate field effect transistor 304. This results in a change in interfacial potential on the gold electrode 311. Potential measurement is carried out by monitoring in real time a change in a current across the source 309 and the drain 310 through the insulated gate field effect transistor 304 before and after the sample solution is filled by the sample injector 307; and thereafter by recording the measured value by means of the signal processing circuit 302 and the data processor 303. The change in the interfacial potential on the gold electrode 311 depends on the concentration of the sodium ion that is the measuring object. Thus, the sodium ion concentration in the sample of unknown concentration can be obtained from the measured potential-change value, based on a calibration curve prepared beforehand through measurement of a standard solution. It is preferable to use the power supply containing alternating current components as the power supply 306, in order to reduce the influence of fluctuation in outer environments under which the measurement is performed. On that occasion, stabilization of the surface potential of the gold electrode 311 can be expected by superimposing an a.c. voltage of 1 kHz or higher on direct current voltage. A syringe pump or a pressure dispensing device can be used as the sample injector 307. An electrode made of other noble metal such as silver or carbon may be used in place of the gold electrode 311. In addition, a straight-chain polymer may be used by physically adsorbed on the gold electrode in order to reduce the influence caused by the adsorption of impurities on the surface of the electrode during biological sample measurement. Methyl cellulose, acrylamide, dextran, polyethylene glycol or the like can be used as the straight-chain polymer without any problems.

The reference electrode 305 applies a potential to be used as the reference, for the purpose of stably measuring the potential change based on an equilibrium reaction or a chemical reaction that occurs on the surface of the gold electrode 311 in the measuring solution 314. Although a silver/silver chloride electrode using saturated potassium chloride for an internal solution or a calomel electrode is typically used as the reference electrode, there is no problem in using the silver/silver chloride electrode alone as a quasi-electrode, in the case where the sample solution to be measured is of fixed composition.

Figure 4:
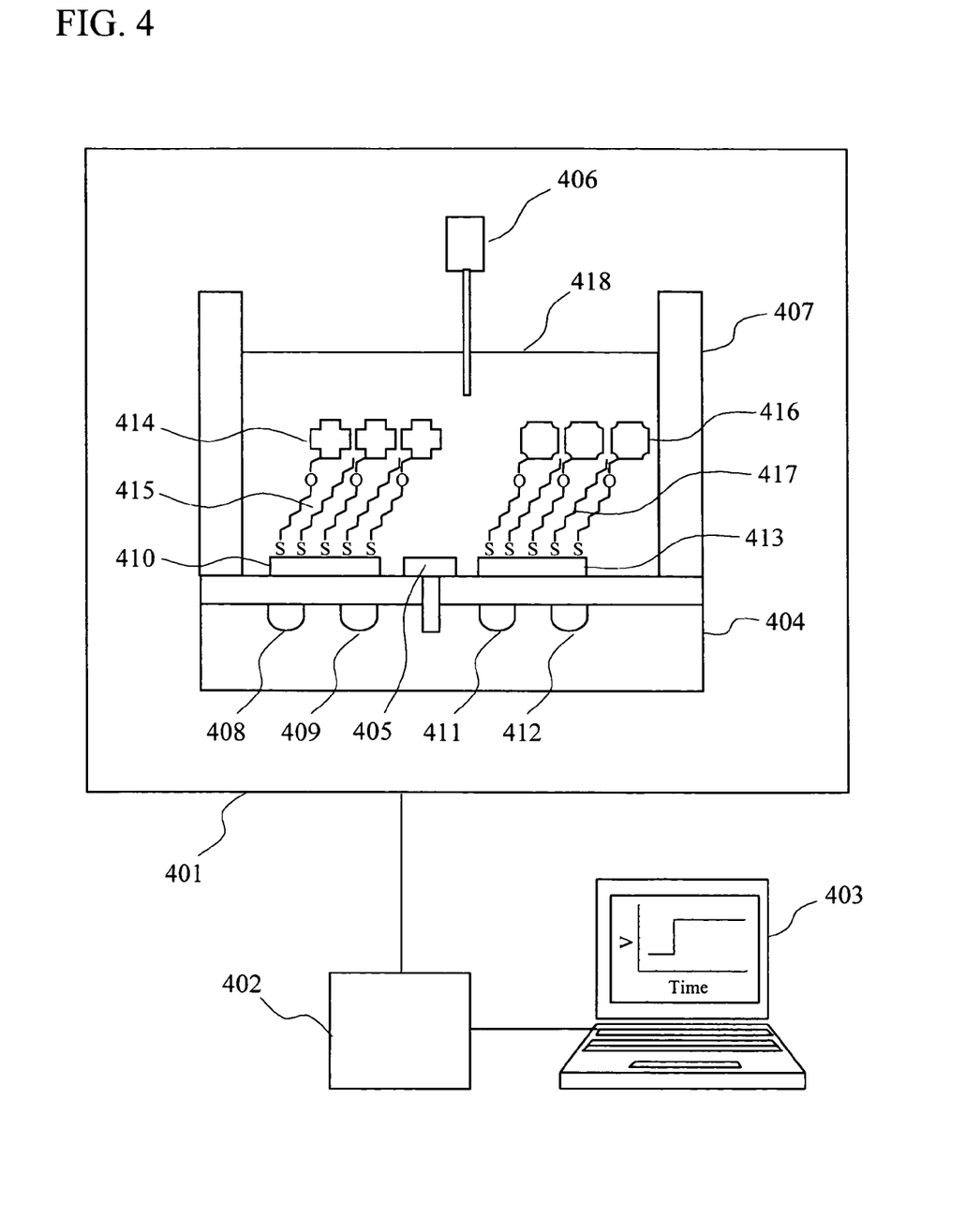
FIG. 4 is a block diagram showing an example of the ion concentration measuring device capable of measuring multiple items at a time, using the FET sensor according to the present invention.

FIG. 4 is a block diagram showing an example of the ion concentration measuring device according to the present invention, capable of measuring multiple items at a time, using the FET sensor. The measuring device of the present invention includes a measuring unit 401, a signal processing circuit 402, and a data processor 403. The measuring unit 401 includes an insulated gate field effect transistor 404, a quasi-reference electrode 405, a sample injector 406 that provides a sample solution containing a measuring substance, and a measuring cell 407. The insulated gate field effect transistor 404 includes multiple sets each of which consists of a unit of a source 408, a drain 409 and a gold electrode 410 having an electrical connection to a gate and a unit of a source 411, a drain 412 and a gold electrode 413 having an electrical connection to a gate. In addition, the quasi-reference electrode 405 is disposed on the same plane as the gold electrodes 410 and 413. The quasi-reference electrode 405 is connected to an external device via conductive wiring. Silver/silver chloride, gold, platinum or the like can be used for the quasi-reference electrode. Crown ether derivatives that act as different cation capturing ligands are immobilized on the gold electrodes 410 and 413, respectively, so as to correspond to multiple items of ions. In this embodiment, a 15-crown-5 derivative 414 that acts as sodium ion capturing ligand and alkanethiol 415 are immobilized on the gold electrode 410; and an 18-crown-6 derivative 416 that acts as potassium ion capturing ligand and alkanethiol 417, on the gold electrode 413. Disposed in a measuring solution 418 within the measuring cell 407 are the gold electrode 410 with the 15-crown-5 derivative 414 that acts as the sodium ion capturing ligand and the alkanethiol 415 immobilized thereon, the gold electrode 413 with the 18-crown-6 derivative 416 that acts as the potassium ion capturing ligand and the alkanethiol 417 immobilized thereon, and the quasi-reference electrode 405.

A measuring procedure is as follows. First, the sample solution is filled into the measuring solution 418 within the measuring cell 407 by use of the sample injector 406. A sodium ion that is a measuring object in the sample solution forms complex, through ion-dipole interaction, with the 15-crown-5 derivative 414 that acts as the sodium ion capturing ligand; and a potassium ion, with the 18-crown-6 derivative 416 that acts as the potassium ion capturing ligand. This results in changes in interfacial potential on the gold electrodes 410 and 413 according to sodium ion concentration and potassium ion concentration, respectively. Potential measurement is carried out by monitoring in real time changes in currents across the source 408 and the drain 409 and across the source 411 and the drain 412 through the insulated gate field effect transistor 404 before and after the sample solution is filled by the sample injector 406; and thereafter by recording the measured values by means of the signal processing circuit 402 and the data processor 403. The concentrations of the sodium ion and the potassium ion that are the measuring objects can be obtained from the measured potential-change values, based on calibration curves prepared beforehand through measurement of a standard solution. On that occasion, a voltage bearing an a.c. voltage of 1 kHz or higher superimposed on direct current voltage is applied to the dummy reference electrode 405 in order to reduce the influence of fluctuation in outer environments under which the measurement is performed. With this application, stabilization of the surface potentials of the gold electrodes 410 and 413 can be expected. A syringe pump or a pressure dispensing device can be used as the sample injector 406. Moreover, electrodes made of other noble metal such as silver or carbon may be used in place of the gold electrodes 410 and 413.

Figure 5A:
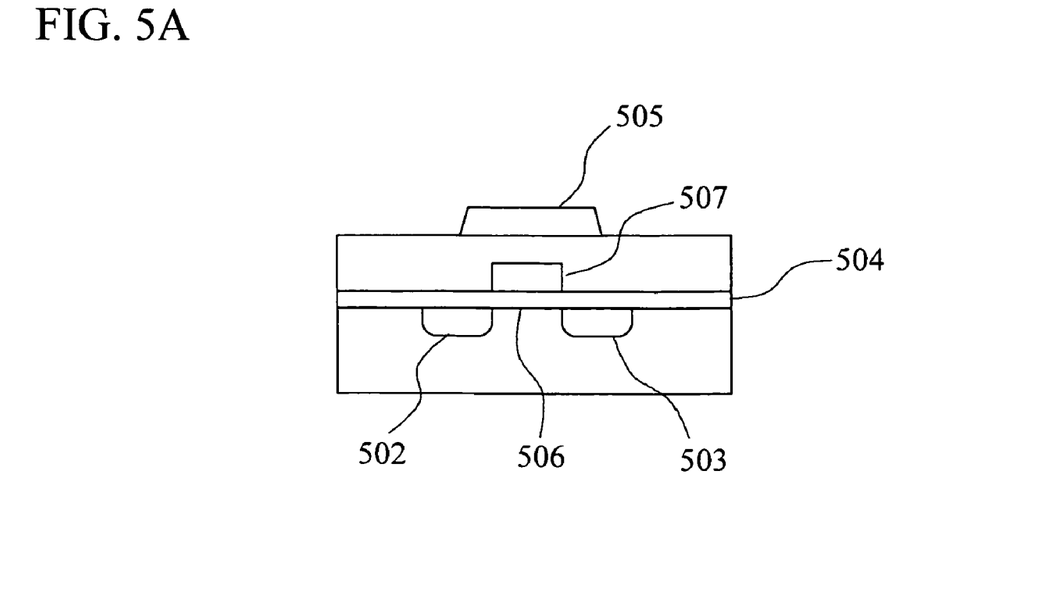
FIGS. 5A and 5B are a cross-sectional view and a plan view, respectively, showing an example of the structure of analytical device for use in the ion concentration measuring device, using the FET sensor of the present invention.
Figure 5B:
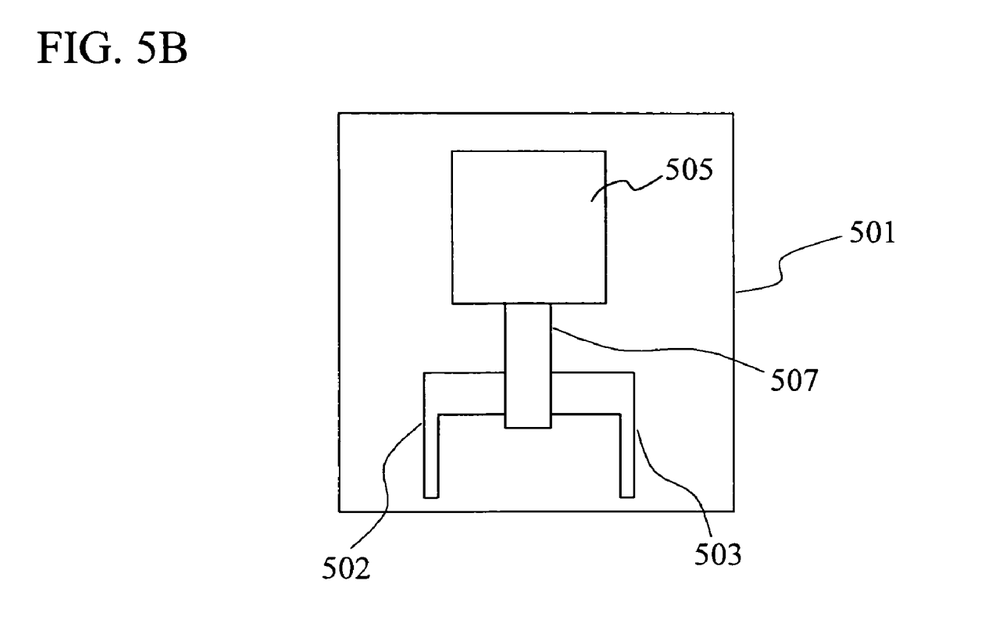

FIGS. 5A and 5B are views showing an example of the structure of analytical devices for use in the ion concentration measuring device, using the FET sensor of the present invention. FIGS. 5A and 5B show a cross-sectional configuration and a plan configuration, respectively. An insulated gate field effect transistor 501 includes a source 502, a drain 503, and a gate insulator 504, which are formed on the surface of a silicon substrate, and is provided with a gold electrode 505. The gold electrode 505 is connected to a gate 506 of the insulated gate field effect transistor by conductive wiring 507. It is preferable to employ a metal-oxide semiconductor field effect transistor (FET) using silicon oxide for an insulating film as the insulated gate field effect transistor. However, a thin film transistor (TFT) may also be used without any problems. Adoption of this structure enables forming the gold electrode 505 in any location and in any size, and further enables changing the volumetric capacity of the measuring cell according to the amount of sample solution targeted for measurement.

The insulated gate field effect transistor employed in this embodiment is a depletion mode FET having an insulating layer using $SiO_2$ (of 17.5 nm in thickness), and the gold electrode is fabricated in dimensions of 400 μm×400 μm. Since an aqueous solution is used for typical measurement, the device has to operate in the solution. For measurement in the solution, it is required to operate within an electrode potential range of −0.5 to 0.5 V, at which an electrochemical reaction is unlikely to occur. In this embodiment, therefore, the fabrication conditions for a depletion mode n-channel type FET, specifically, ion implantation conditions for threshold voltage (Vt) control, is adjusted so that the threshold voltage of the FET is set in the vicinity of −0.5 V. Incidentally, an electrode made of other noble metal such as silver may also be used in place of the gold electrode. The device having two or more FET sensors on the same substrate is fabricated by forming multiple FET sensors, one of which is shown in FIGS. 5A and 5B, on the same substrate. Crosstalk between the FET sensors, which becomes a problem on that occasion, can be suppressed by employing an SOI (silicon on insulator) structure.

Description will be given with reference to other embodiments with regard to the advantageous effect of immobilizing the alkanethiol that acts as the insulating molecule having a longer carbon chain than that of the linker, while coexisting with the crown ether derivative, when immobilizing the crown ether derivative that acts as the cation capturing ligand on the surface of the gold electrode, through the linker that acts as the insulating molecule.

The immobilization of the ligand on the surface of the gold electrode was performed by the following procedure. First, the gold electrode for use in the immobilization was cleaned in turn with a 1N nitric acid, deionized water and ethanol, and the surface of the gold electrode was purged with nitrogen. Then, the gold electrode was immersed for an hour in a mixed solution of the ligand and the alkanethiol (concentration: 0.5 mM; solvent: ethanol). After the completion of the immobilization, the gold electrode underwent heat treatment at 95 degrees C. for ten minutes in a 0.1-M sodium sulfate solution. After that, the gold electrode was cleaned with ethanol and deionized water, and was preserved in a 300 mM sodium chloride aqueous solution until just before use.

Figure 6:
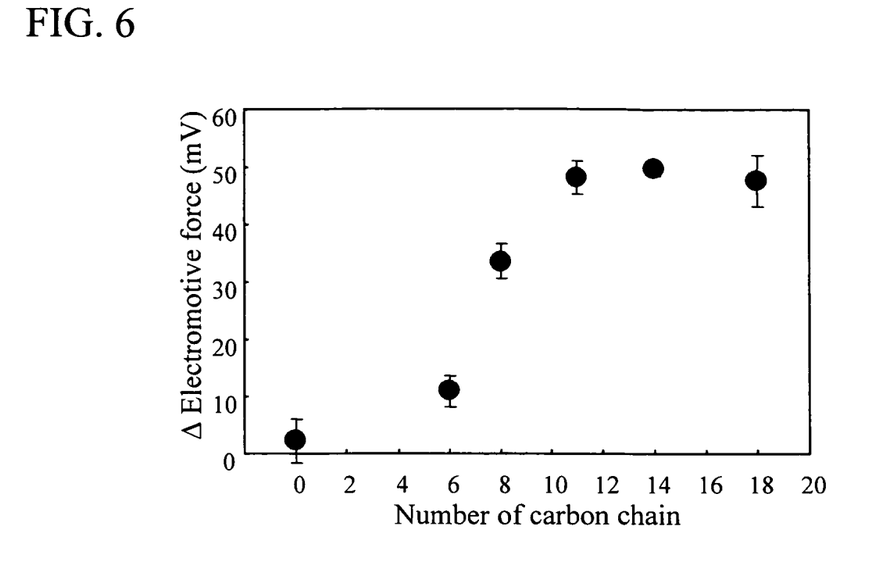
FIG. 6 is a plot showing the influence of the length of carbon chain of alkanethiol coexisting with the ligand on potential response to sodium ion concentration.

FIG. 6 shows the influence of the length of carbon chain of the alkanethiol coexisting with the ligand on potential response to the sodium ion concentration. The potential response to the sodium ion concentration was measured using a sodium chloride aqueous solution, and slope sensitivity (namely, electromotive force on the surface of the electrode) was compared in a concentration range of 4.5 mM to 300 mM. Note that, the measured potential value is the value measured five minutes after immersion. In this embodiment, 2-[(6-mercaptohexyl)oxy]methyl-(15-crown-5), which is an example of the 15-crown-5 derivative using 1-hexanethiol as the linker, was used as the ligand for the sodium ion, and 1-hexanethiol (1-HT), 1-octanethiol (1-OT), 1-undecanethiol (1-UDT), 1-tetradecanethiol (1-TDT), and 1-octadecanethiol (1-ODT), which are hydrophobic alkanethiol, were used as the alkanethiol.

As shown in FIG. 6, the slope sensitivity of the sodium ion electrode, having the alkanethiol with the different length of carbon chain coexisted therewith and immobilized thereon, became higher as the length of carbon chain of the alkanethiol coexisting became longer. When the number of carbon atoms was equal to or larger than eleven, the slope sensitivity was held constant (specifically, at about 50 mV/decade). This is possibly because of the fact that the alkanethiol fills a gap between the crown ether derivatives and hence inhibits the entry of ions. Meanwhile, when the number of carbon atoms was equal to or larger than eighteen, the potential became unstable. This is possibly because of the fact that, when the length of carbon chain of the alkanethiol becomes too long, another gap develops in the crown ether derivative. It is desired that the length of the alkanethiol be equal to the height of the crown ether. In the case of this embodiment, the crown ether is equivalent in length to three to four carbon atoms, and therefore, 1-TDT having thirteen to fourteen carbon atoms is the optimum alkanethiol, allowing for the length of carbon chain bonded to the ligand and an ether bond length. Generally, the alkanethiol having the carbon chain equivalent in length to the total length of the crown ether and the linker bonded to the crown ether can be used. Meanwhile, the alkanethiol in which the number of carbon atoms is larger than eighteen has the problem of having difficulty in immobilization, because of the carbon chains getting entangled with each other or doing the like.

Figure 7:
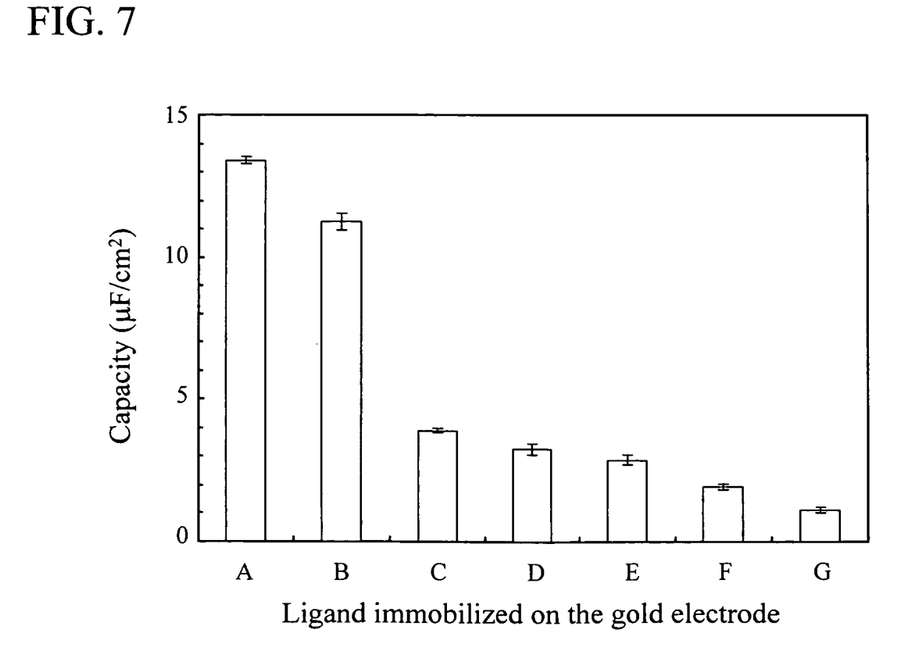
FIG. 7 is a graph showing an improvement in shielding properties on the surface of the gold electrode caused by the coexistence of the alkanethiol with the ligand, by comparing electric capacity on the surface of a gold electrode.

A comparison was made of electric capacity on the surface of the gold electrode, for showing an improvement in shielding properties on the surface of the gold electrode, caused by the coexistence of the alkanethiol with the ligand (see FIG. 7). 2-[(6-mercaptohexyl)oxy]methyl-(15-crown-5), which is the mono-crown ether derivative, was used as the ligand. On the horizontal axis of FIG. 7, A represents the gold electrode having nothing immobilized thereon; B, the gold electrode having the ligand alone immobilized thereon; C, the gold electrode having the ligand and 1-HT immobilized thereon; D, the gold electrode having the ligand and 1-OT immobilized thereon; E, the gold electrode having the ligand and 1-UDT immobilized thereon; F, the gold electrode having the ligand and 1-TDT immobilized thereon; and G, the gold electrode having the ligand and 1-ODT immobilized thereon. In the case of the gold electrode having the ligand alone immobilized thereon, the electric capacity decreased by about 16%, as compared to the surface of the gold electrode having nothing immobilized thereon. When the number of carbon atoms of the alkanethiol coexisting was equal to eighteen, the electric capacity decreased to $1/10$ or less. It is possible that the gold electrode, using the ligand having the 15-crown-5 derivative employed at this time bonded thereto, increased in electric capacity as compared to the gold electrode having typical alkanethiol immobilized thereon, since a crown ether ring was larger than a distance between self-assembled monolayers and thus resulted in the presence of a gap between the immobilized molecules. Generally, the immobilization density of the self-assembled monolayers using the alkanethiol is $4.4 \times 10^{14}$ molecules/cm$^2$; however, in the case of the gold electrode having 2-[(6-mercaptohexyl) oxy]methyl-(15-crown-5) alone immobilized thereon, the measured value of the immobilization density of the self-assembled monolayers is $2.9 \pm 0.27$ molecules/cm$^2$. Thus, there is a slight gap. It is possibly because a decrease in the electric capacity on the surface of the gold electrode, as mentioned above, led to enhancement of the shielding properties and hence to an improvement in the slope sensitivity.

Figure 8:
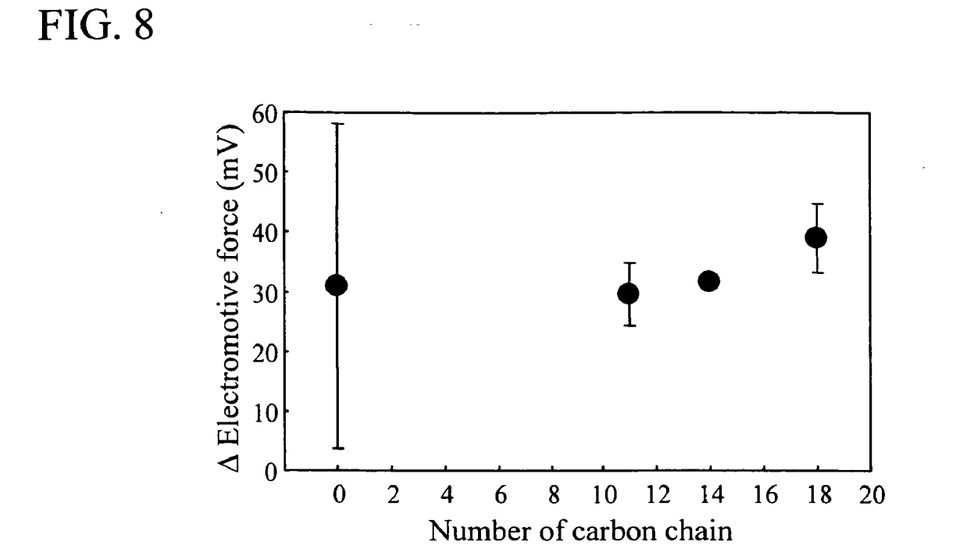
FIG. 8 is a plot showing the influence of the length of carbon chain of the alkanethiol coexisting with different ligand having a different linker length, on the potential response to the sodium ion concentration.

FIG. 8 shows the influence of the length of carbon chain of the alkanethiol coexisting with different ligand having a different linker length, on the potential response to the sodium ion concentration. The potential response to the sodium ion concentration was measured using a sodium chloride aqueous solution, and the slope sensitivity was compared in a concentration range of 4.5 mM to 300 mM. Incidentally, the measured potential value is the value five minutes after immersion. In this embodiment, 2-[10-mercaptodecyl)oxy]methyl-(15-crown-5) in which the number of carbon atoms of the linker is ten was used as the ligand for the sodium ion, and 1-undecanethiol (1-UDT), 1-tetradecanethiol (1-TDT), and 1-octadecanethiol (1-ODT), which are hydrophobic alkanethiol, were used as the alkanethiol. As shown in FIG. 8, the slope sensitivity of the sodium ion electrode, having the alkanethiol with the different length of carbon chain coexisted therewith and immobilized thereon, became higher as the length of carbon chain of the alkanethiol coexisting became longer. 2-[10-mercaptodecyl)oxy]methyl-(15-crown-5) in which the number of carbon atoms of the linker is ten, even with the use of the ligand alone, could achieve an improvement in the slope sensitivity to some extent, as compared to 2-[(6-mercaptohexyl)oxy]methyl-(15-crown-5) in which the number of carbon atoms of the linker is six. It is possibly because longer carbon chain of the linker led to a reduction in the influence of the gap between the crown ether derivatives.

Figure 9:
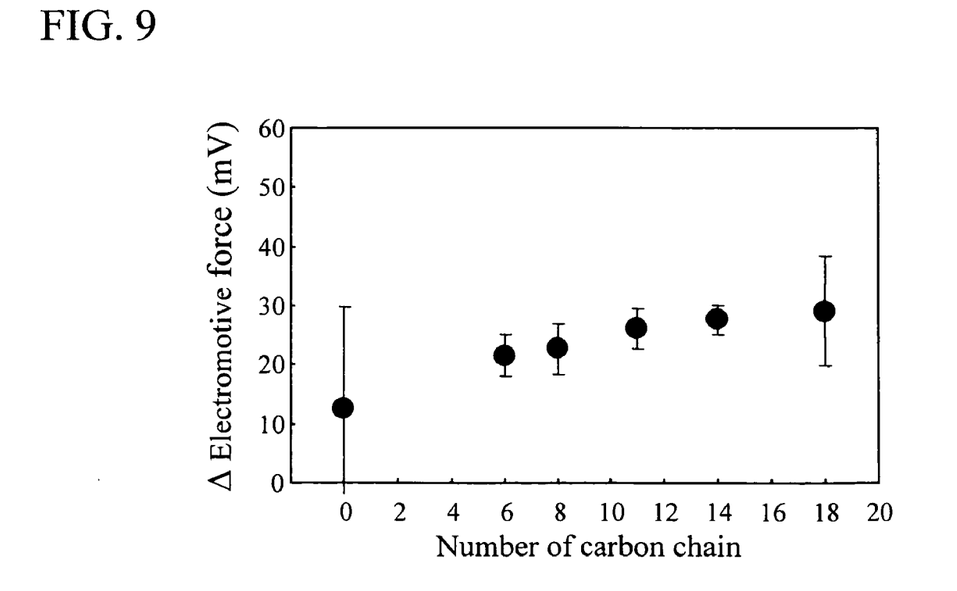
FIG. 9 is a plot showing the influence of the length of carbon chain of the alkanethiol coexisting with the ligand on the potential response to the sodium ion concentration.

FIG. 9 shows the influence of the length of carbon chain of the alkanethiol coexisting with different ligand on the potential response to the sodium ion concentration. The potential response to the sodium ion concentration was measured using a sodium chloride aqueous solution, and the slope sensitivity was compared in a concentration range of 4.5 mM to 300 mM. Incidentally, the measured potential value is the value five minutes after immersion. In this embodiment, di(1,4,7,10-tetraoxacyclododecan-2-ylmethyl)methyl(6-sulfanylhexyl), which is an example of the bis-crown ether derivative, was used as the ligand for the sodium ion, and 1-hexanethiol (1-HT), 1-octanethiol (1-OT), 1-undecanethiol (1-UDT), 1-tetradecanethiol (1-TDT), and 1-octadecanethiol (1-ODT), which are hydrophobic alkanethiol, were used as the alkanethiol. As shown in FIG. 9, the slope sensitivity of the sodium ion electrode, having the alkanethiol with the different length of carbon chain coexisted therewith and immobilized thereon, became higher as the length of carbon chain of the alkanethiol coexisting became longer, as in the case of the mono-crown ether derivative. As mentioned above, with the use of any of the mono-crown ether derivative and the bis-crown ether derivative, the length of carbon chain of the alkanethiol coexisting is made longer than the length of carbon chain of the linker added to the ligand to thereby achieve an improvement in the slope sensitivity to the sodium ion concentration.

Figure 10A:
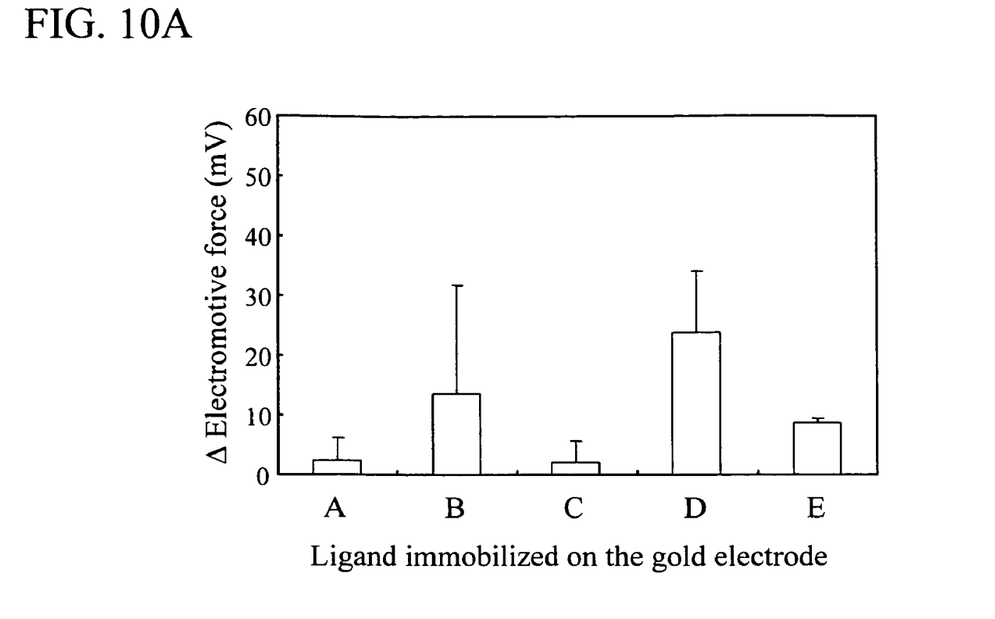
FIGS. 10A and 10B are graphs showing the influence of charge at the end of the alkanethiol coexisting with the ligand on the potential response to the sodium ion concentration.
Figure 10B:
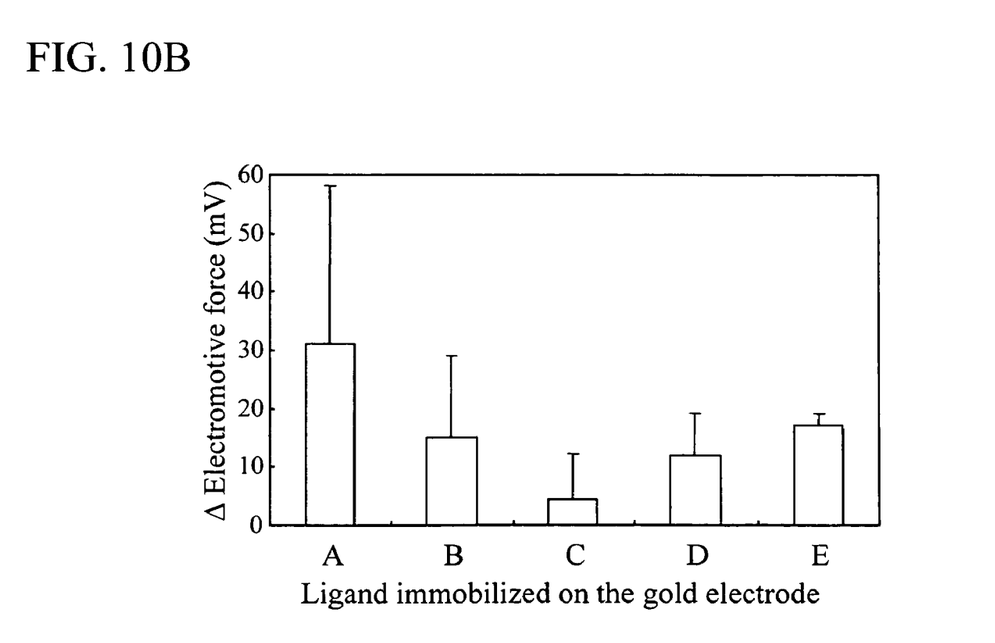

Description will be given below with regard to the influence of charge of the alkanethiol immobilized on the surface of the gold electrode, coexisting with the crown ether derivative that acts as the cation capturing ligand. FIGS. 10A and 10B show the influence of the charge at the end of the alkanethiol coexisting with the ligand on the potential response to the sodium ion concentration. The potential response to the sodium ion concentration was measured using a sodium chloride aqueous solution, and the slope sensitivity was compared in a concentration range of 4.5 mM to 300 mM. Incidentally, the measured potential value is the value five minutes after immersion.

FIG. 10A shows the slope sensitivity observed in the case where 2-[(6-mercaptohexyl)oxy]methyl-(15-crown-5) in which the number of carbon atoms of the linker is six was used as the ligand for the sodium ion, and 6-hydroxy-1-hexane thiol (6-HHT) having a hydroxy group at the end, 6-amino-1-hexane thiol (6-AHT) having an amino group at the end, 5-carboxy-1-pentane thiol (5-CPT) having a carboxyl group at the end, and triethyleneglycol-mono-11-mercaptodecylether (TGM) having hydrophilic ethylene glycol, in which the number of carbon atoms is eighteen, were used as the alkanethiol. On the horizontal axis of FIG. 10A, A represents the gold electrode having the ligand alone immobilized thereon; B, the gold electrode having the ligand and 6-HHT immobilized thereon; C, the gold electrode having the ligand and 6-AHT immobilized thereon; D, the gold electrode having the ligand and 5-CPT immobilized thereon; and E, the gold electrode having the ligand and TGM immobilized thereon.

FIG. 10B shows the slope sensitivity observed in the case where 2-[10-mercaptodecyl)oxy]methyl-(15-crown-5) in which the number of carbon atoms of the linker is ten was used as the ligand for the sodium ion, and 11-hydroxy-1-undecanethiol (11-HUT) having a hydroxy group at the end, 11-amino-1-undecanethiol (11-AUT) having an amino group at the end, 10-carboxy-1-decanethiol (10-CDT) having a carboxyl group at the end, and triethyleneglycol-mono-11-mercaptodecylether (TGM) having hydrophilic ethylene glycol, in which the number of carbon atoms is eighteen, were used as the alkanethiol. On the horizontal axis of FIG. 10B, A represents the gold electrode having the ligand alone immobilized thereon; B, the gold electrode having the ligand and 11-HUT immobilized thereon; C, the gold electrode having the ligand and 11-AUT immobilized thereon; D, the gold electrode having the ligand and 10-CDT immobilized thereon; and E, the gold electrode having the ligand and TGM immobilized thereon.

As shown in FIG. 10A, in the case of the ligand in which the number of carbon atoms of the linker is six, the loading of electric charge into the end of the alkanethiol leads to an improvement in the slope sensitivity, but the level of the slope sensitivity was equivalent to or lower than that observed at the coexistence of 1-HT having six carbon atoms. The slope sensitivity observed at the coexistence of TGM in which the number of carbon atoms is equivalent to eighteen was ⅕ or lower of the slope sensitivity observed at the coexistence of 18-ODT having the same length of carbon chain. In the case of the ligand in which the number of carbon atoms of the linker is ten, the same trend was observed as shown in FIG. 10B. In all cases, the loading of electric charge into the end of the alkanethiol coexisting led to a reduction in the slope sensitivity, as compared to the use of the ligand alone. The slope sensitivity observed at the coexistence of TGM in which the number of carbon atoms is equivalent to eighteen was also ½ or lower of the slope sensitivity observed at the coexistence of 18-ODT having the same length of carbon chain. As shown in FIGS. 6, 8, 10A and 10B, the loading of a hydrophilic group bearing electric charge into the alkanethiol coexisting with the ligand leads to a reduction in the slope sensitivity to the sodium ion concentration. In other words, it is desirable that the alkanethiol coexisting with the sodium ion capturing ligand be hydrophobic and have a longer carbon chain than that of the linker of the sodium ion capturing ligand.

Figure 11A:
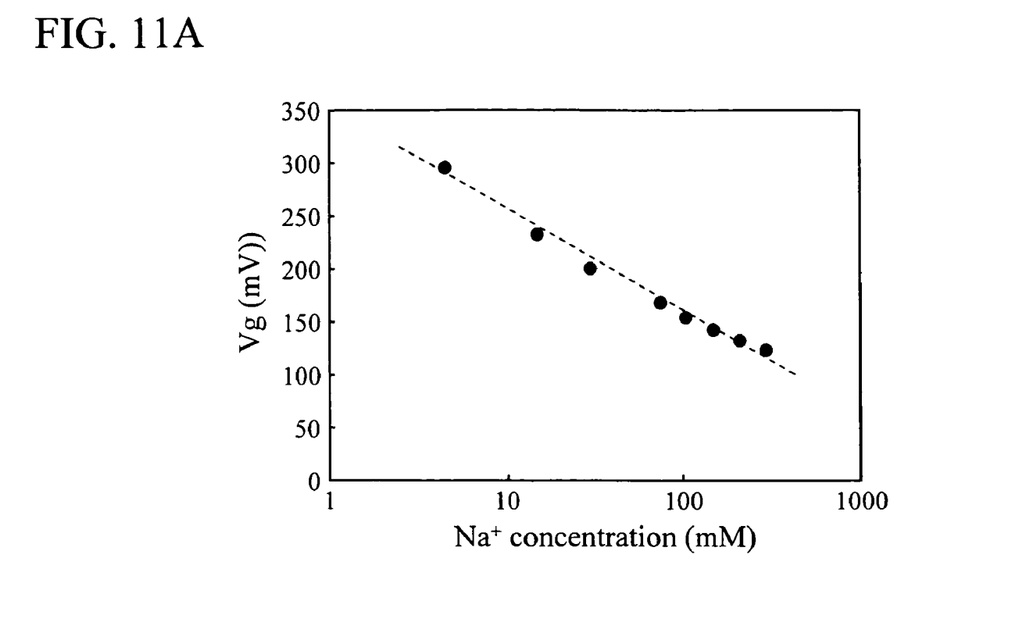
FIGS. 11A and 11B are plots showing the potential response to the sodium ion concentration indicating the effect of the application of an a.c. voltage to the FET sensor, respectively showing the measured result of the potential response to the sodium ion concentration obtained under the application of the a.c. voltage to the FET sensor, and the measured result of the potential response to the sodium ion concentration obtained by a typical potentiometer.
Figure 11B:
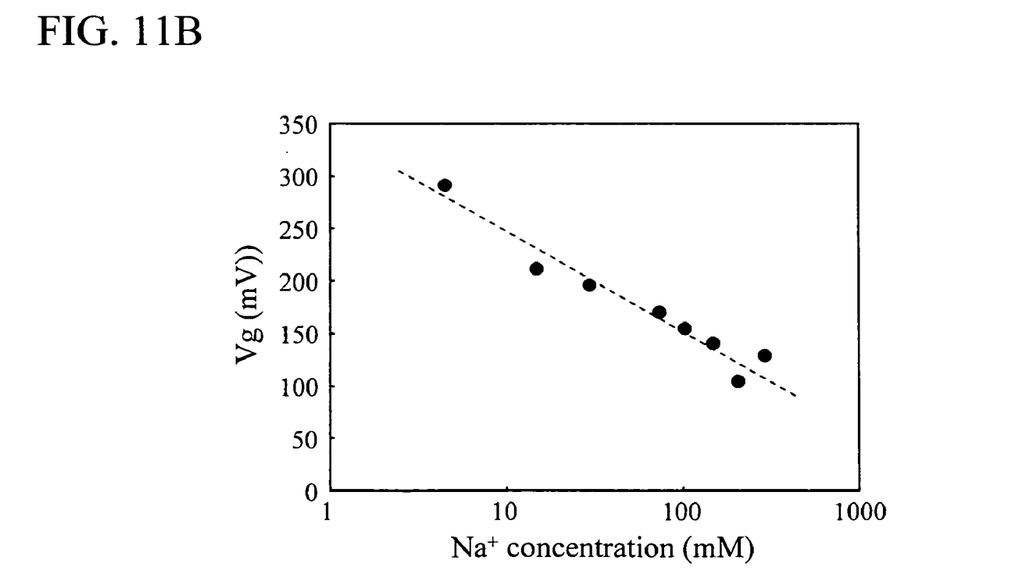

Description will be given with reference to other embodiments with regard to the effect of the application of the a.c. voltage to the FET sensor of the present invention. FIG. 11A shows the potential response to the sodium ion concentration in a case where an alternating current having a frequency of 1 MHz, a center voltage of 100 mV and an amplitude voltage of 200 mV is applied to the reference electrode so as to observe the effect of the application of the a.c. voltage to the FET sensor. The potential response to the sodium ion concentration was measured using a sodium chloride aqueous solution, and the slope sensitivity was compared in a concentration range of 4.5 mM to 300 mM. Incidentally, the measured potential value is the value five minutes after immersion. In this embodiment, 2-[(6-mercaptohexyl)oxy]methyl-(15-crown-5), which is an example of the 15-crown-5 derivative, was used as the ligand for the sodium ion, and 1-octadecanethiol (1-ODT), which is hydrophobic alkanethiol, was used as the alkanethiol. The current/voltage characteristic of the transistor were measured by using a semiconductor parameter analyzer (e.g., Agilent 4155C Semiconductor Parameter Analyzer), and by calculating a gate voltage (Vg) from a current/voltage characteristic curve of the pre-acquired FET. FIG. 11B shows the potential response to the sodium ion concentration in the case of applying a d.c. voltage to the reference electrode, as a reference test, for observing the effect of the application of the a.c. voltage. The potential response (correlation coefficient: $R^2=0.979$) observed in the case of superimposing a high frequency voltage on the reference electrode varied little and was stable, as compared to the potential response (correlation coefficient: $R^2=0.944$) in the case of applying the d.c. voltage to the reference electrode.

Description will be given with reference to other embodiments with regard to the effect of the application of the a.c. voltage to the FET sensor of the present invention.

Figure 12A:
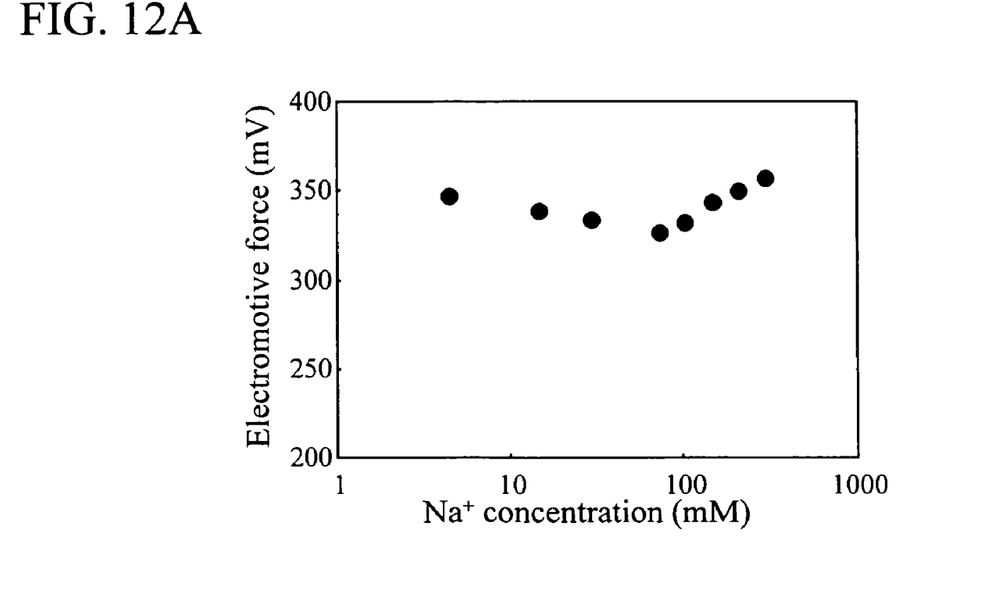
FIGS. 12A and 12B are plots showing the potential response to the sodium ion concentration indicating the effect of the application of the a.c. voltage to the FET sensor, respectively showing the measured result of the potential response to the sodium ion concentration obtained by the typical potentiometer, and the measured result of the potential response to the sodium ion concentration obtained under the application of the a.c. voltage to the FET sensor.
Figure 12B:
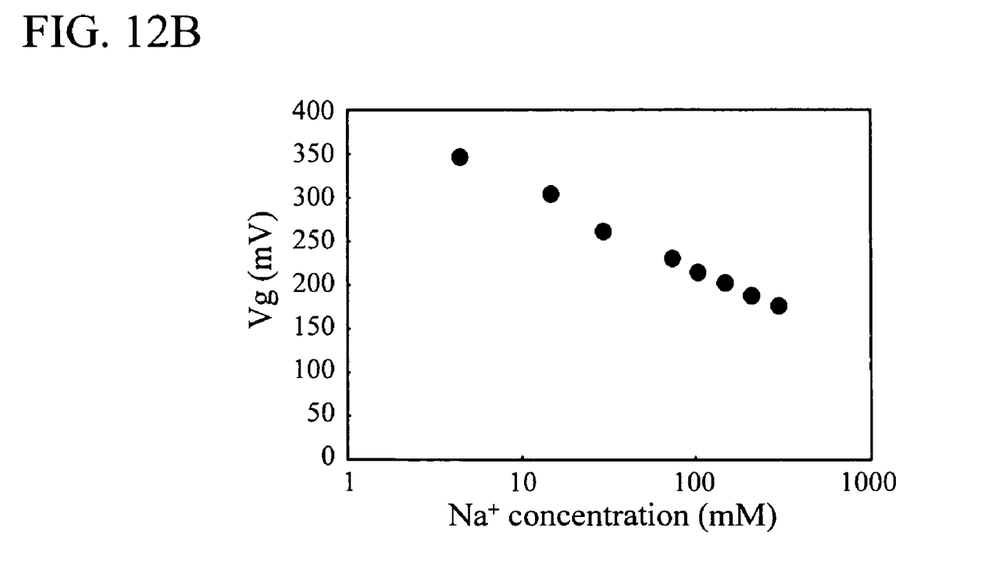

In order to examine the effect of a combination of the FET sensor and a measurement technique applying a superimposed high-frequency voltage, a comparison was made in measuring the ion electrode having 2-[(6-mercaptohexyl)oxy]methyl-(15-crown-5) alone, which is an example of the 15-crown-5 derivative being the mono-crown ether derivative, immobilized as the ligand for the sodium ion on the surface of the gold electrode, between a result obtained by a typical potentiometer and a result obtained by applying the a.c. voltage to the FET sensor. FIGS. 12A and 12B show the potential response to the sodium ion concentration measured by the typical potentiometer, and by applying the a.c. voltage to the FET sensor, respectively. As shown in FIG. 12A, in the case of the measurement by the typical potentiometer shown in FIG. 1, the potential response to the sodium ion concentration behaved differently when the sodium ion concentration became high (specifically, about 100 mM or higher).

Figure 13A:
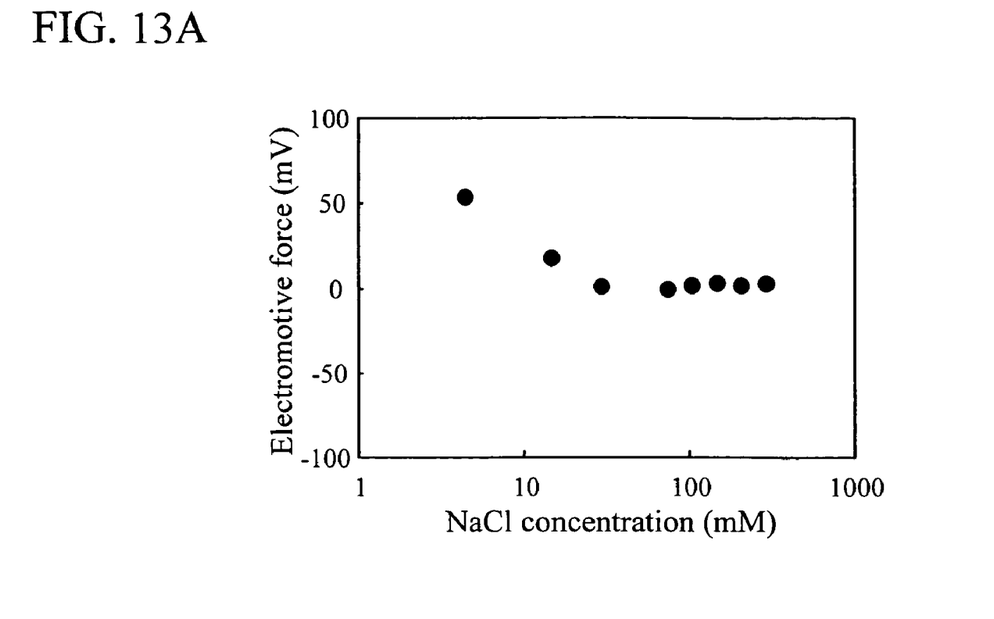
FIGS. 13A and 13B are plots showing the potential response to the sodium ion concentration indicating the effect of the application of the a.c. voltage to the FET sensor, respectively showing the measured result of the potential response to the sodium ion concentration obtained by the typical potentiometer, and the measured result of the potential response to the sodium ion concentration obtained under the application of the a.c. voltage to the FET sensor.
Figure 13B:
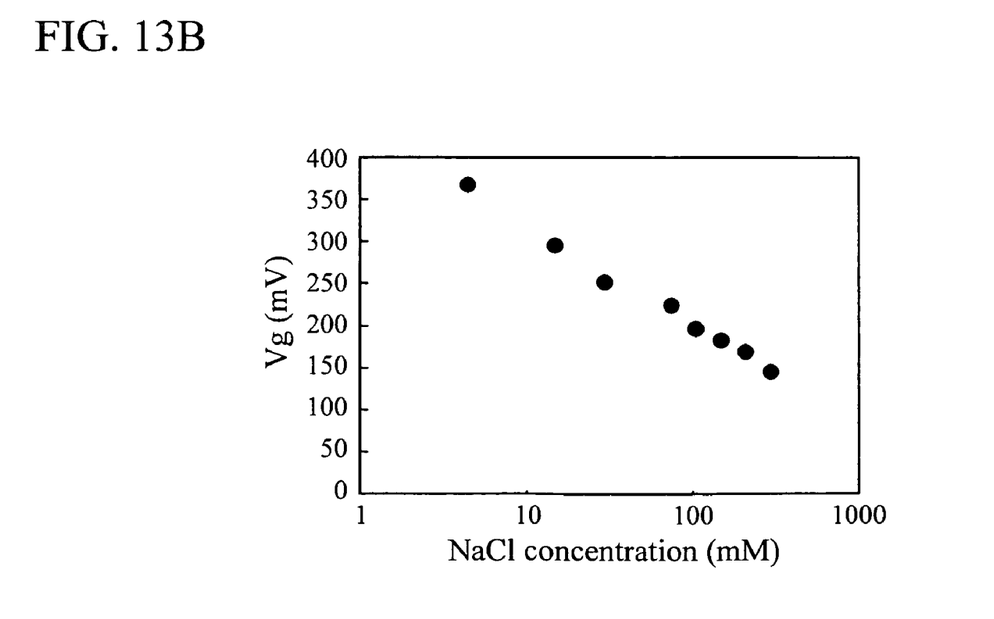

On the other hand, in the case of the measurement by applying the a.c. voltage to the FET sensor, good potential response to the sodium ion concentration was achieved, as shown in FIG. 12B. Also, a comparison was made in measuring the ion electrode having di(1,4,7,10-tetraoxacyclododecan-2-ylmethyl)methyl(6-sulfanylhexyl) alone, which is an example of the bis(12-crown-4) derivative being the bis-crown ether derivative, immobilized as the ligand for the sodium ion on the surface of the gold electrode, between a result obtained by the typical potentiometer and a result obtained by applying the a.c. voltage to the FET sensor. FIGS. 13A and 13B show the potential response to the sodium ion concentration measured by the typical potentiometer, and by applying the a.c. voltage to the FET sensor, respectively. As shown in FIG. 13A, in the case of the measurement by the typical potentiometer shown in FIG. 1, the potential response to the sodium ion concentration behaved differently when the sodium ion concentration became high (specifically, about 70 mM or higher).

On the other hand, in the case of the measurement by applying the a.c. voltage to the FET sensor, good potential response to the sodium ion concentration was achieved, as shown in FIG. 13B. In this embodiment, the a.c. voltage having a frequency of 1 MHz is applied to the reference electrode; however, an a.c. voltage having a frequency of 1 kHz or higher may also be applied without any problems. These results are possibly because of the following factors: in the case of typical potential measurement, when the sodium ion concentration becomes high, the ion enters into the gap between the crown ether derivatives and thus the potential becomes unstable; meanwhile, the application of the high frequency superimposition method to the FET sensor inhibits the entry of the ion into the gap between the crown ether derivatives and thus makes the potential stable. As mentioned above, the insulated gate field effect transistor formed on the same substrate as the gold electrode is used as the potentiometer, and, during measurement, a high frequency of 1 kHz or higher is superimposed on the reference electrode. This enables accurate measurement of a reaction process (i.e., the capture of ions) that occurs on the gold electrode. Moreover, a straight-chain polymer may also be used by physically adsorbed on the gold electrode in order to reduce the influence caused by the adsorption of impurities on the surface of the electrode during biological component measurement.

What is claimed is:

1. An ion concentration measuring device, comprising:
   a cell into which a measuring solution containing a target substance is introduced;
   a field effect transistor;
   an ion selective gold electrode in contact with the measuring solution in the cell, the ion selective electrode being connected to a gate of the field effect transistor by wiring;
   a reference electrode in contact with the measuring solution in the cell;
   a power supply that applies a voltage to the reference electrode;
   a detector that detects an output from the field effect transistor; and
   a bonded substance composed of a first insulating molecule comprising an alkanethiol and bonded to a crown ether derivative, the bonded substance being immobilized on a surface of the ion selective electrode via a bond between a thiol group of the alkanethiol of the first insulating molecule and gold of the ion selective gold electrode.

2. The ion concentration measuring device according to claim 1, wherein a second insulating molecule is immobilized on the ion selective gold electrode.

3. The ion concentration measuring device according to claim 2, wherein the length of carbon chain of the second insulating molecule is longer than the length of carbon chain of the first insulating molecule.

4. The ion concentration measuring device according to claim 2, wherein the second insulating molecule is an alkanethiol.

5. The ion concentration measuring device according to claim 1, wherein the ion selective electrode is made of any one of noble metal and carbon.

6. The ion concentration measuring device according to claim 1, wherein any one of sodium ion, potassium ion and lithium ion concentrations is measured.

7. The ion concentration measuring device according to claim 1, wherein the power supply applies an alternating voltage.

8. The ion concentration measuring device according to claim 1, wherein the power supply applies an alternating voltage having a frequency of 1 kHz or higher.

9. The ion concentration measuring device according to claim 1, wherein the reference electrode is formed on the same substrate as the field effect transistor.

10. The ion concentration measuring device according to claim 1, further comprising two or more field effect transistors and the reference electrode located on the same substrate.

11. An ion concentration measuring element, comprising:
    a field effect transistor; and
    an ion selective gold electrode having a bonded substance composed of a first insulating molecule comprising an alkanethiol and bonded to a crown ether derivative, the bonded substance immobilized on a surface of the ion selective electrode via a bond between gold of the ion selective electrode and a thiol group of the alkanethiol of the first insulating molecule,
    wherein the ion selective gold electrode is connected to a gate of the field effect transistor by a conductive wiring.

12. The ion concentration measuring element according to claim 11, wherein the bonded substance of the first insulating molecule and the crown ether derivative, and a second insulating molecule having a longer carbon chain than the first insulating molecule, are immobilized, coexisting together, on the ion selective electrode.

13. The ion concentration measuring element according to claim 12, wherein the second insulating molecule is an alkanethiol.

14. The ion concentration measuring element according to claim 11, further comprising two or more field effect transistors, the ion selective electrode and the reference electrode located on the same substrate.

15. The ion concentration measuring element according to claim 11, wherein the ion selective electrode is made of any one of noble metal and carbon.

* * * * *